(12) United States Patent
Crook et al.

(10) Patent No.: US 8,968,994 B2
(45) Date of Patent: Mar. 3, 2015

(54) METHOD FOR STEM CELL CULTURE AND CELLS DERIVED THEREFROM

(76) Inventors: Jeremy Micah Crook, Helios (SG); Rachel Horne, Helios (SG); Blaine Wesley Phillips, Helios (SG)

( * ) Notice: Subject to any disclaimer, the term of this patent is extended or adjusted under 35 U.S.C. 154(b) by 855 days.

(21) Appl. No.: 12/307,684

(22) PCT Filed: Jul. 6, 2007

(86) PCT No.: PCT/SG2007/000201
§ 371 (c)(1),
(2), (4) Date: Jan. 6, 2009

(87) PCT Pub. No.: WO2008/004990
PCT Pub. Date: Jan. 10, 2008

(65) Prior Publication Data
US 2009/0311735 A1    Dec. 17, 2009

Related U.S. Application Data

(60) Provisional application No. 60/818,780, filed on Jul. 6, 2006.

(51) Int. Cl.
*C12Q 1/00*    (2006.01)
*C12N 5/0735*    (2010.01)

(52) U.S. Cl.
CPC .......... *C12N 5/0606* (2013.01); *C12N 2531/00* (2013.01); *C12N 2533/20* (2013.01); *C12N 2533/32* (2013.01)
USPC ............................................. 435/4; 435/7.21

(58) Field of Classification Search
CPC ............................ C12N 15/00; C12N 15/1034
USPC .................................................. 435/4, 7.21
See application file for complete search history.

(56) References Cited

U.S. PATENT DOCUMENTS

| | | |
|---|---|---|
| 6,378,527 B1 | 4/2002 | Hungerford et al. |
| 6,875,607 B1 | 4/2005 | Reubinoff et al. |
| 2006/0136068 A1 | 6/2006 | De Bruijn et al. |

FOREIGN PATENT DOCUMENTS

| | | |
|---|---|---|
| WO | WO 03/039575 A2 | 5/2003 |

OTHER PUBLICATIONS

Maida et al. "Expansion of bovine chondrocytes on microcarriers enhances redifferentiation", Tissue Engineering, 2003, 9(5):939-948.*
Abdallah et al. "Regulation of human skeletal stem cells differentiation by Dlk1/Pref-1", J of Bone Mineral Res., 2004, 19(5):841-852.*
Hillex data sheet: 2007, 2 pages.*
Stewart et al. "Manipulation of human pluripotent embryonal carcinoma stem cells and the development of neural subtypes", Stem Cells, 2003, 21:248-256.*
Horrocks et al. "Formation of neurosphores from human embryonal carcinoma stem cells" BBRC, 2003, 304:411-416.*
Murashov et al. "17beta-estradiol enhances neuronal differentiation of mouse embryonic stem cells", FEBS Letters, 2004, 569:165-168.*
Khademhosseini et al. "Layer-by-layer deposition of hyaluronic acid and poly-L-lysine for patterned cell co-cultures", Biomaterials, 2004, 25:3583-3592.*
Maguire et al. "Alginate-PLL microencapsulation: effect on the differentiation of embryonic stem cells into hepatocytes", Biotechnology and Bioengineering, 2006, 93(3):581-591.*
Peng, et al. "Neural precursors derived from human embryonic stem cells", Science in China Ser. C Life Sciences, 2005, 48(3):295-299.*
Constantinescu et al "Lamin A/C expression is a marker of mouse and human embryonic stem cell differentiation", Stem Cells, 2006, 24:177-185.*
Salli et al. "Serotonin neurons derived from rhesus monkey embryonic stem cells: similarities to CNS serotonin neurons", Experimental Neurology, 2004, 188:351-364.*
Li, M.C. et al., "Isolation and Characterization of Brain Tumor Stem Cells in Human Medulloblastoma" Chinese Journal of Cancer (2006) pp. 241-246, vol. 25(2).
Fok, Y. et al., "Shear-Controlled Single-Step Mouse Embryonic Stem Cell Expansion and Embryoid Body-Based Differentiation" Stem Cells (2005) pp. 1333-1342, vol. 23.
Kato, D. et al., "The Design of Polymer Microcarrier Surfaces for Enhanced Cell Growth" Biomaterials (2003) pp. 4253-4264, vol. 24.
Frauenschuh, S. et al., "A Microcarrier-Based Cultivation System for Expansion of Primary Mesenchymal Stem Cells" Biotechnology Progress (2007) pp. 187-193, vol. 23(1).
Chen G. et al., "Hybrid Biomaterials for Tissue Engineering: A preparative Method for PLA or PLGA-Collagen Hybrid Sponges", *Advanced Materials* 12(6): 455-457 (2000).
Himes V. B. et al., "Attachment and Growth of Mammalian Cells on Microcarriers with Different Ion Exchange Capacities", *Biotechnology and Bioengineering* 29: 1155-1163 (1987).
Levine D. W. et al., "Optimization of Growth Surface Parameters in Microcarrier Cell Culture", *Biotechnology and Bioengineering* 21: 821-845 (1979).
Zwaka and Thomson (2005) "A germ cell origin of embryonic stem cells?" Development 132(2):227.
Thomson (1998) "Embryonic stem cells derived from human blastocysts" Science 282:1145.

* cited by examiner

*Primary Examiner* — Bin Shen
(74) *Attorney, Agent, or Firm* — E. Stewart Mittler

(57) ABSTRACT

There is described a method of promoting the attachment, survival and/or proliferation of a stem cell in culture, the method comprising culturing a stem cell on a positively-charged support surface. There are also provided a cell composition prepared according to the method of the invention.

13 Claims, 12 Drawing Sheets

A

B

METHOD FOR STEM CELL CULTURE AND CELLS DERIVED THEREFROM

Figure 1:
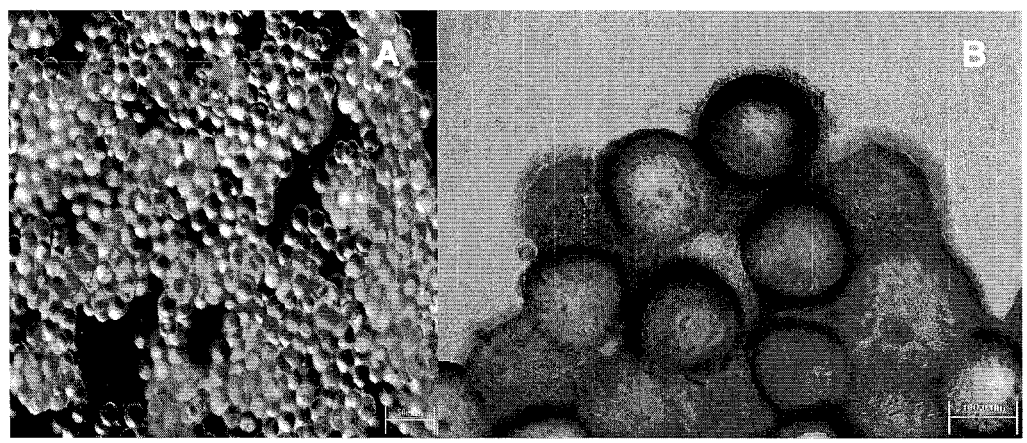
Figure 1:
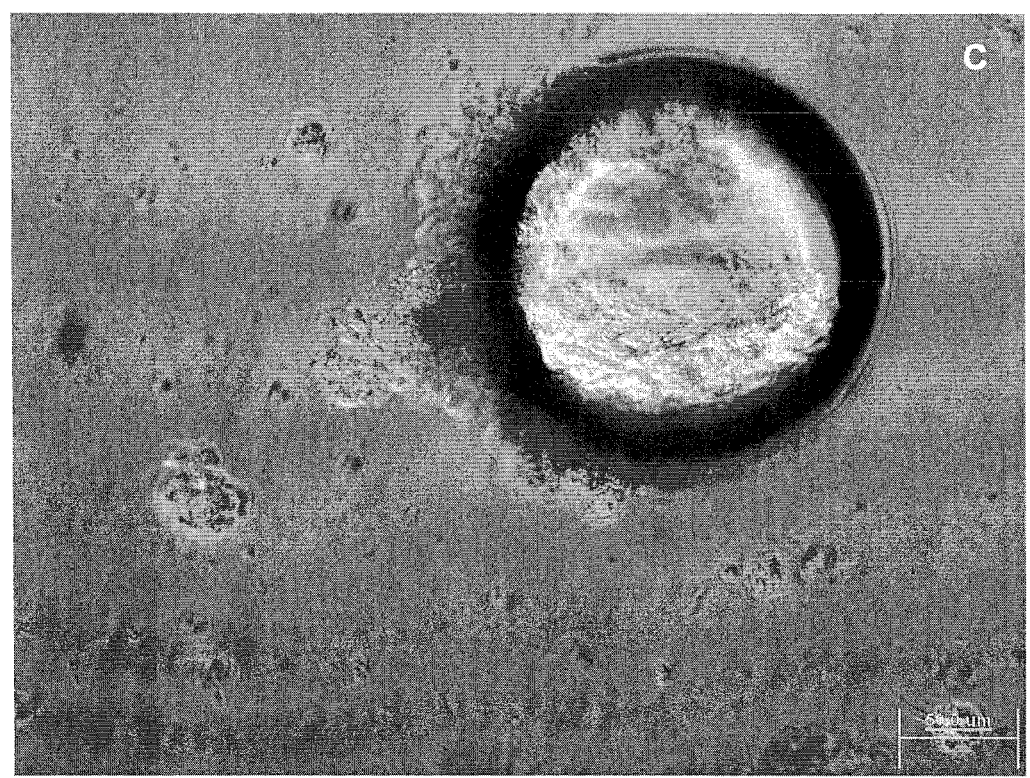

This application claims the benefit of U.S. Provisional Application No. 60/818,780 filed on Jul. 6, 2006.

The present invention relates generally to methods of culturing stem cells in the absence of a feeder cell. More specifically, the present invention relates to a method of culturing a stem cell in vitro on a positively-charged support surface. The present invention also relates to cell compositions derived from such methods and uses thereof.

BACKGROUND

Stem cells are undifferentiated, or immature, cells that are capable of giving rise to multiple, specialized cell types and ultimately to terminally differentiated cells. Unlike any other cells, they are able to renew themselves such that essentially an endless supply of mature cell types can be generated when needed. Due to this capacity for self-renewal, stem cells are therapeutically useful for the regeneration and repair of tissues. Stem cells have the potential for providing benefit in a variety of clinical settings.

Embryonic stem cells are stem cells from embryos which are capable of differentiation into most, if not all, of the differentiated cell types of a mature body. Stem cells are referred to as pluripotent, which describes this capability of differentiating into many cell types. A category of pluripotent stem cell of high interest to the research community is the human embryonic stem cell, abbreviated here as human ES cell, which is an embryonic stem cell derived from a human embryonic source. Human embryonic stem cells are of great scientific interest because they are capable of indefinite proliferation in culture and are thus capable, at least in principle, of supplying cells and tissues for replacement of failing or defective human tissue. For this reason, the existence in culture of human embryonic stem cells offers the potential of unlimited amounts of human cells and tissues for use in a variety of therapeutic protocols to assist in human health. It is envisioned that human embryonic stem cells will be proliferated and directed to differentiate into specific lineages so as to develop differentiated cells or tissues which can be transplanted into human bodies for therapeutic purposes. Human embryonic stem cells and the differentiated cells that may be derived from them are also powerful scientific tools for the study of human cellular and developmental systems. However, the limitation of many of these potential applications has been obtaining a sufficient number of stem cells and stimulating terminal differentiation of these stem cells into mature tissue-specific cells.

The basic techniques used for the generation and culture of stem cells, particularly embryonic stem cells, required the use of mouse embryonic fibroblast (MEF) feeder cells as a feeder layer on which stem cells could be cultured. The fibroblast feeder cells act to encourage the stem cells to remain in an undifferentiated state. Whilst such techniques do work, there are also significant limitations and drawbacks to the procedures currently employed. For instance, there are significant concerns that one or more agents, such as a virus, could be transmitted from the feeder cells to the stem cells in culture.

Therefore, if one of the objectives of stem cell cultures is to create tissues which can ultimately be transplanted into a human body, it is highly desirable that the stem cells are never exposed to cells of another species or to cells derived from another individual. Accordingly, establishing a cell culture environment that will permit the proliferation and culture of stem cells in an undifferentiated or a substantially undifferentiated state in the absence of a feeder layer is of great interest in the continued development of techniques for the long term culture of human embryonic stem cells, as well as meeting the regulatory requirements for producing clinically acceptable stem cells, such as the generation and storage of a Master Cell Bank comprising a homogeneous population of human embryonic stem cells produced from a single cell source. Compliance with the aforementioned criteria will ensure quality assurance and safety towards maximizing clinical efficacy, the primary mandate for the Food and Drug Administration (FDA) and other such regulatory bodies. A suitable stem cell culture method that satisfies existing and future regulations under Good Tissue Practice (GTP) and Good Manufacturing Practice (GMP) will also be essential to the manufacture and use of viable material for cell based therapy. Thus, a standardized and scaleable procedure with validated and non-adventitious components is highly advantageous.

The present invention overcomes, or at least alleviates, some of the aforementioned problems of the art by providing a method of culturing a stem cell in the absence of feeder cells and preferably without relying on an ECM (or a similar growth matrix) culture platform.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, the present invention provides a method of promoting the attachment, survival and/or proliferation of a stem cell in culture, the method comprising culturing a stem cell on a positively-charged support surface.

In a second aspect of the present invention, there is provided a cell composition that comprises a population of undifferentiated or substantially undifferentiated stem cells derived by culturing a stem cell in accordance with the methods of the present invention.

In a third aspect of the present invention, there is provided a composition of differentiated or substantially differentiated stem cells derived by subjecting the population of undifferentiated or substantially undifferentiated stem cells derived from the methods of the present invention to conditions that will promote the differentiation of the stem cells towards a required lineage.

In a fourth aspect of the present invention, there is provided a method of engineering a biological tissue, the method comprising the step of directing the differentiation of the undifferentiated or substantially undifferentiated stem cells derived from the methods of the present invention towards a required lineage so as to form the biological tissue.

In a fifth aspect of the present invention, there is provided a method of using stem cells that have been cultured in accordance with the methods of the present invention for cell transplantation or to engineer tissues to treat various disorders or diseases, including (but not limited to) those of the cardiovascular system, muscle, ligament, bone, tendon, cartilage, nervous system, blood, immune system, liver, or pancreas.

In a sixth aspect of the present invention, there is provided a method for identifying a test sample containing an agent or factor that modulates the attachment, survival, proliferation and/or differentiation of a stem cell, the method comprising the steps of (a) contacting the stem cell with (i) a positively-charged support surface and (ii) a test sample suspected of including the agent or factor and (b) measuring the attachment, survival, proliferation and/or differentiation of the stem cell compared to the attachment, survival, proliferation and/or differentiation of a similar stem cell in a culture in the absence of the test sample.

In a seventh aspect of the present invention, there is provided a kit for promoting the attachment, survival and/or proliferation of a stem cell, the kit comprising (a) a positively-charged support surface and (b) at least one component or reagent suitable for culturing stem cells in an aqueous environment capable of supporting the attachment, survival and/or proliferation of the stem cells.

In an eighth aspect of the present invention, there is provided a conditioned medium derived by culturing a stem cell on a positively-charged support surface.

In a ninth aspect of the present invention, there is provided a cell culture system comprising stem cells cultured on positively-charged support surface.

FIGURES

FIG. 1 shows gross morphology of a human embryonic stem cell (hES) cell culture following propagation on cationic amine tri-methylamine coated microcarriers. Representative bright field low (A), medium (B) and high (C) powered photomicrographs illustrating attachment and culture of day 7 hES-2 on cationic amine tri-methylamine coated microcarriers.

Figure 2:
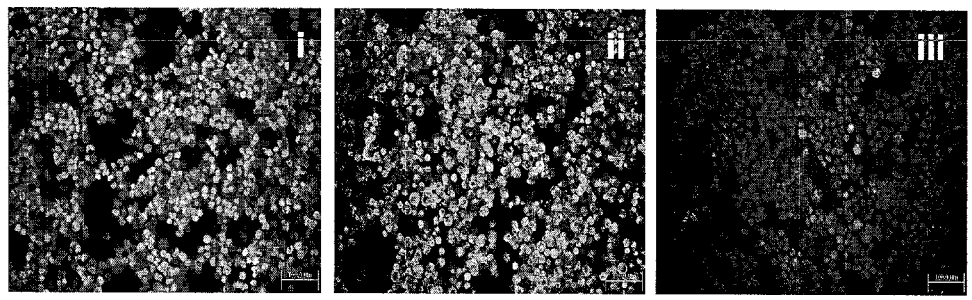
Figure 2:
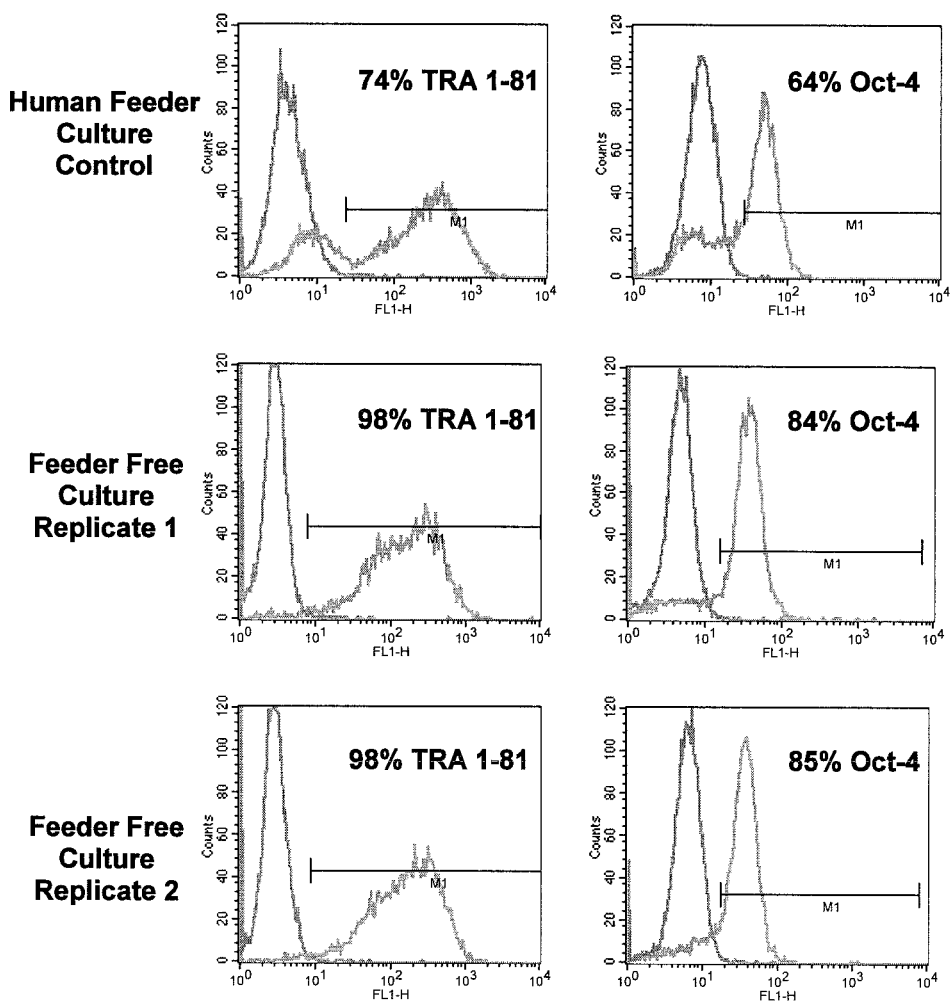

FIG. 2 shows an immunohistochemical analysis (A) and flow cytometric analysis (B) of the hES cell status following propagation on cationic amine tri-methylamine coated microcarriers. Representative photomicrographs (A) illustrating attachment and maintenance of Oct-4 (i) and TRA 1-81 (ii) positive, and SSEA-1 (iii) negative hES-2 cells to cationic amine tri-methylamine coated microcarriers (green labeling: specific markers of interest, blue staining: DAPI). Representative histogram plots (B) derived from gated events illustrate cell number (Y-axis) and TRA 1-81 and Oct-4 labeling (X-axis) of hES-2 cells following 3 weeks of culture through 3 passages.

Figure 3:
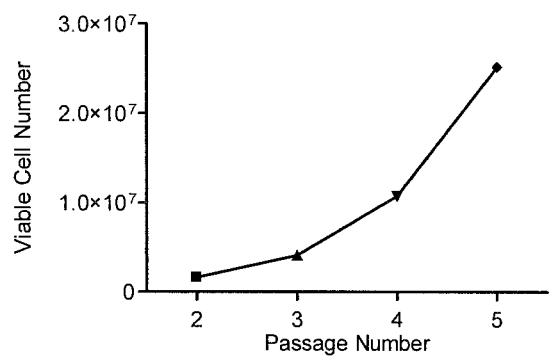
Figure 3:
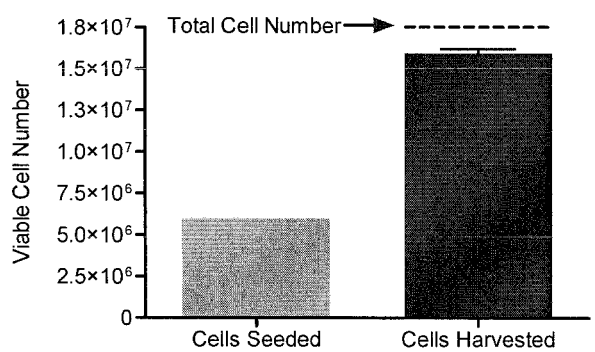
Figure 3:
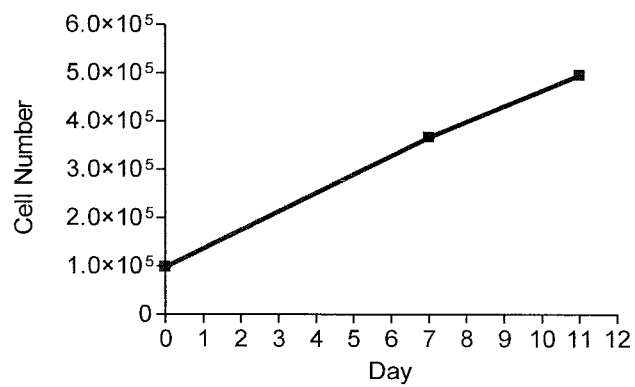

FIG. 3 shows hES cell expansion by propagation on cationic amine tri-methylamine coated microcarriers in bulb stirred culture vessels (A and B) or on Cytodex 1 microcarriers consisting of a cross linked dextran matrix substituted with cationic N,N-diethylaminoethyl groups in flat bed culture plates (C). Growth profile of hES-2 cultured over 5 weeks through 5 passages is shown in (A) and the growth profile of hES-2 cultured over 4 weeks through 4 passages is shown in (B). Growth profile of hES-2 cultured for 11 days on positively charged Cytodex-1 microcarrier beads is shown in (C).

Figure 4:
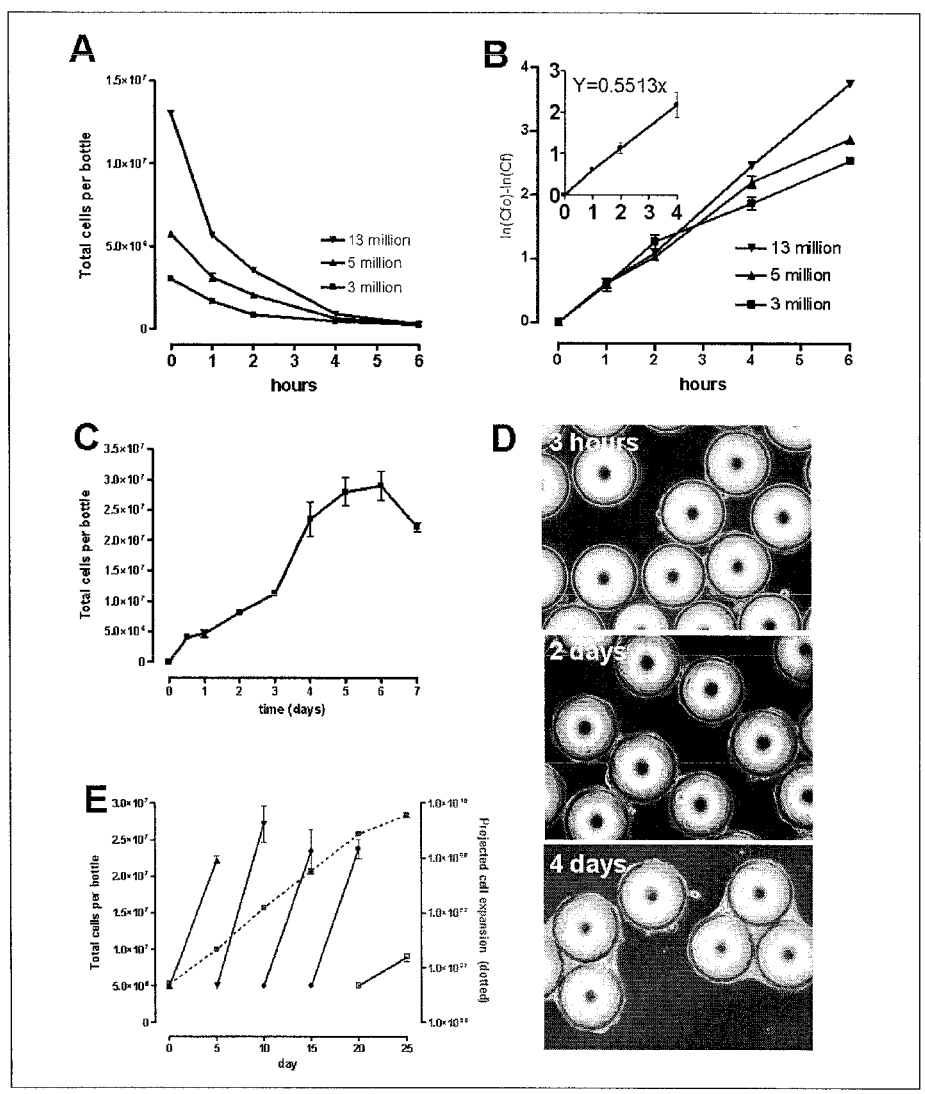

FIG. 4 shows expansion of GMP-compliant human foreskin fibroblasts (Ortec International) capable of supporting pluripotent hES cell growth. The figure describes the attachment and growth kinetics of human fibroblasts onto cationic amine tri-methylamine coated microcarriers. Depletion of free cells is seen within the medium as the cells adhere to the microcarriers with first order kinetics (A). Confirmation of first order kinetics is seen in (B) and the standard growth kinetics of the fibroblasts is shown in (C). Morphology of the cells and their attachment at various time points is seen in (D). Multi-passage expansion of the passage 7 (P7) fibroblast cells in medium containing tri-methylamine microcarriers is shown in (E). The solid lines represent expansion during each individual passage and the dotted lines represent cell expansion based on the approximate 4-5 fold split ratio.

Figure 5:
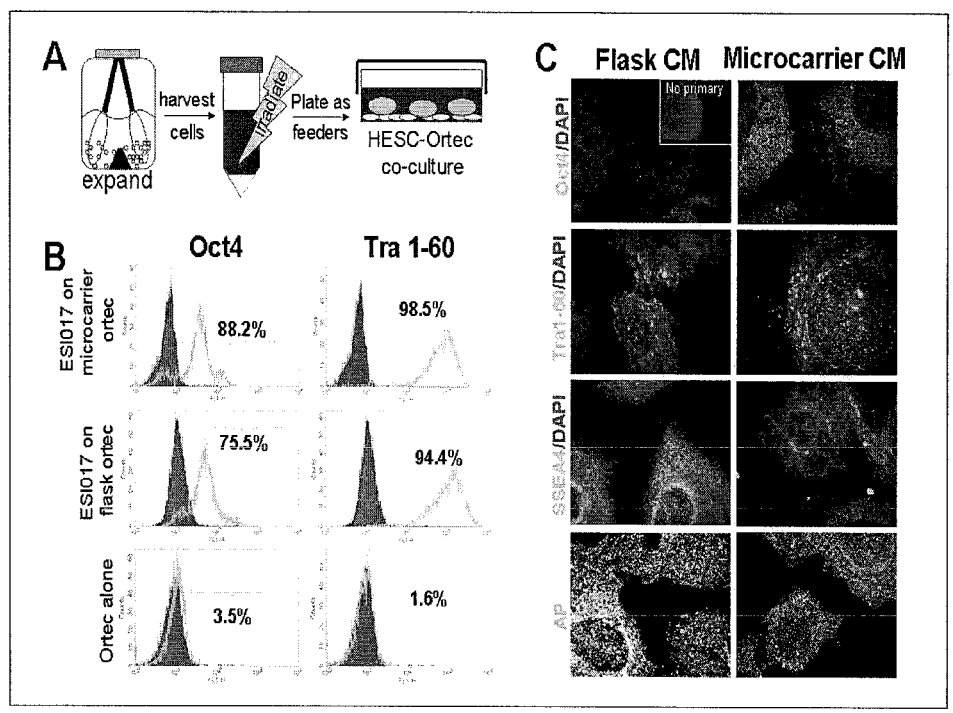

FIG. 5 shows the microcarrier-expanded human fibroblasts supporting pluripotent growth of ESI-017 hES cells in co-cultures. Schematic of cell expansion and harvesting of P7 human fibroblasts as feeders for ESI-017 co-cultures is shown in (A). ESI-017 cells cultured for at least 5 passages on the microcarrier-expanded fibroblast cells were analysed for pluripotency markers, Oct4 and Tra 1-60 by flow cytometry as shown in (B) and immunophenotypic analysis was done for Oct4, Tra 1-60 and SSEA4 expression, with a comparison to control (flask-expanded fibroblasts) cells as shown in (C). The cells were also tested for alkaline phosphatase activity, an additional marker of pluripotency (C). Representative histogram plots derived from gated events in flow cytometric analysis illustrate cell number (Y-axis) and TRA 1-81 and Oct-4 labelling (X-axis) (B) and green labelling represent specific markers of interest, blue staining represent DAPI in immunohistochemical analysis.

Figure 6:
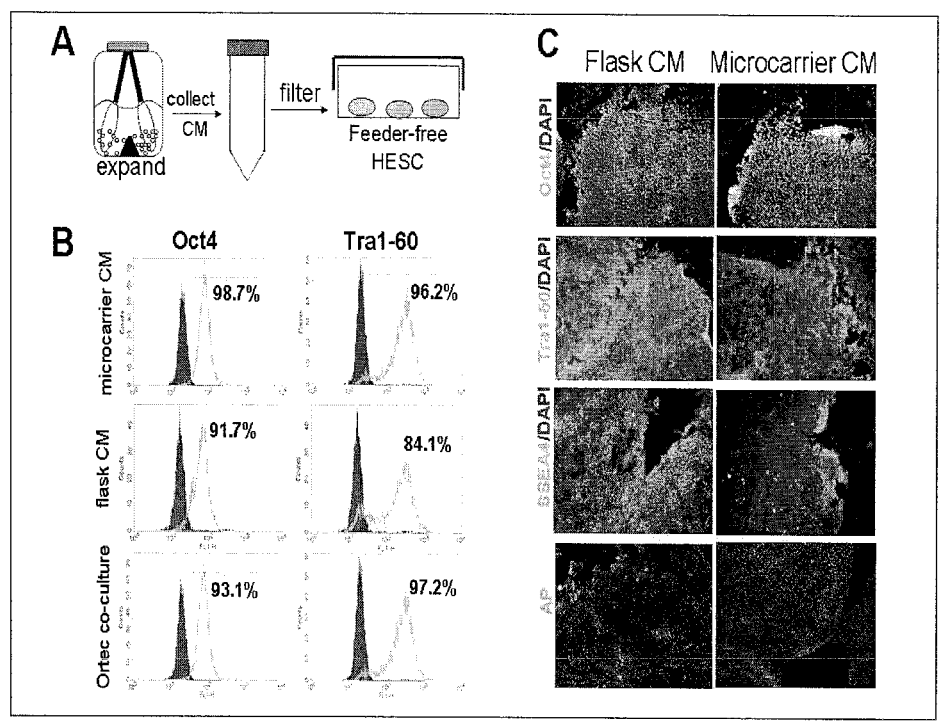

FIG. 6 shows the capacity of the conditioned medium (CM) from microcarrier-expanded human fibroblasts in supporting pluripotent growth of ESI-017 cells grown under feeder free conditions. Schematic of fibroblast expansion and conditioned medium harvesting from suspension cultures is shown in (A). Flow cytometry assessment (B) of pluripotency markers Oct4 and Tra1-60 expression by ESI-017 cells expanded in feeder-free conditions with CM generated from flat-bed cultured human fibroblasts (flask CM) or from microcarrier-expanded human fibroblasts (microcarrier CM) and assessment for pluripotency markers Oct4, Tra1-60 and SSEA4 by immunohistochemistry (C). The cells were also tested for alkaline phosphatase activity, an additional marker of pluripotency (C). Representative histogram plots derived from gated events in flow cytometric analysis illustrate cell number (Y-axis) and TRA 1-81 and Oct-4 labelling (X-axis) (B) and green labeling represent specific markers of interest, blue staining represent DAPI in immunohistochemical analysis.

Figure 7:
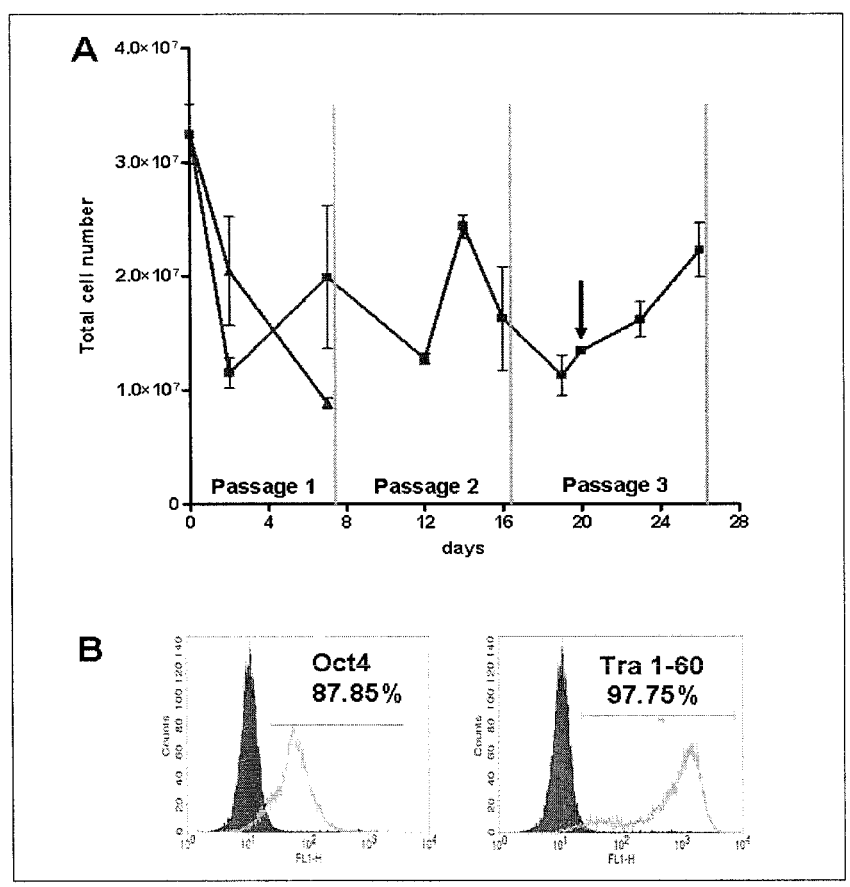

FIG. 7 shows the expansion of ESI-017 hES cells on cationic amine tri-methylamine coated microcarriers in an aggregate or clump-based multi passaging culture. Graph representing the culture of ESI-017 hES cells on microcarriers over 3 passages is shown in (A). Cells harvested on day 20 were analyzed for pluripotency markers Oct-4 positive and Tra1-60 expression by flow cytometry as shown in (B). Representative histogram plots derived from gated events in flow cytometric analysis illustrate cell number (Y-axis) and TRA 1-81 and Oct-4 labeling (X-axis) (B).

Figure 8:
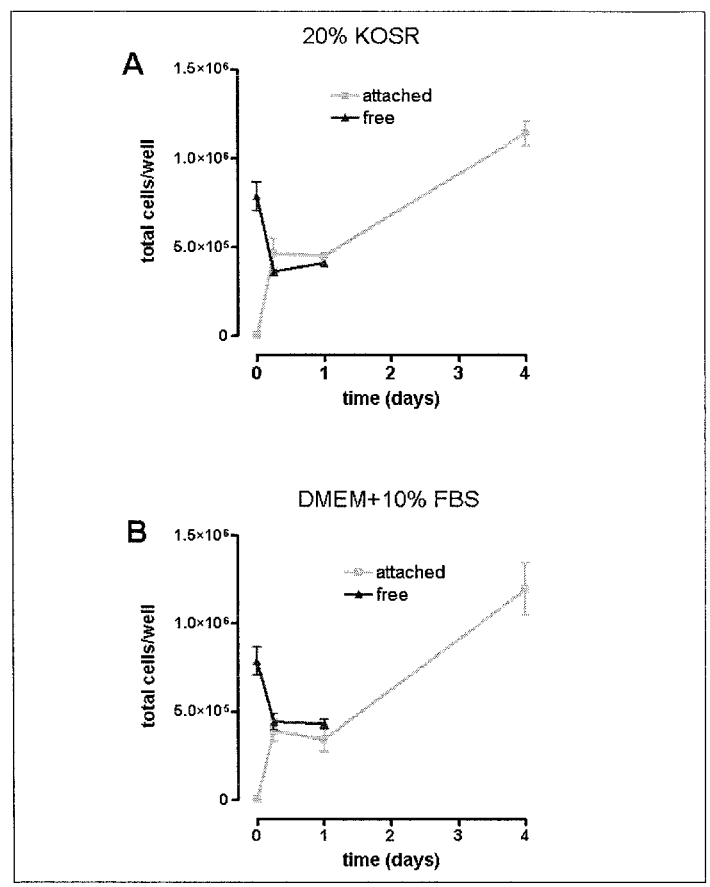

FIG. 8 shows the expansion of ESI-017 hES cells on cationic amine tri-methylamine coated microcarriers in different types of culture medium over several days. Expansion of ESI-017 hES cells on Hillex II microcarriers in human fibroblast conditioned 20% KOSR medium (A) and expansion of ESI-017 hES cells on Hillex II microcarriers in DMEM+FBS medium (B).

Figure 9:
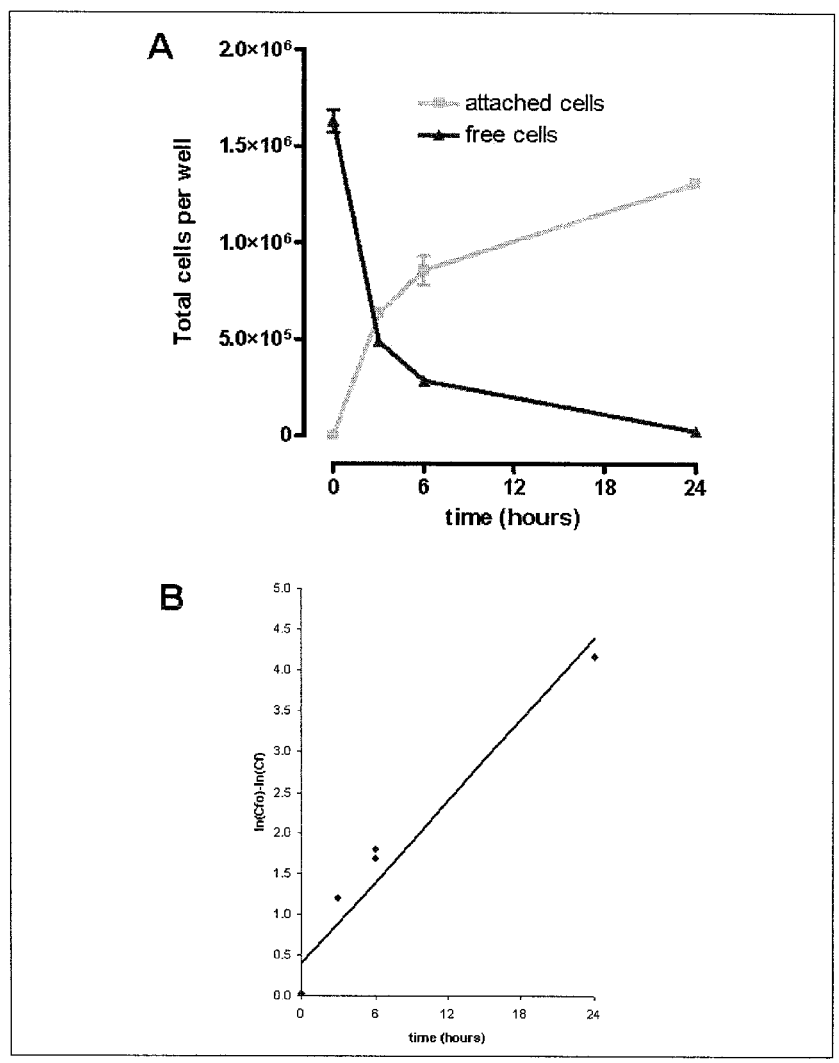

FIGS. 9(A) and (B) shows the growth kinetics of ESI-017 on cationic amine tri-methylamine coated microcarriers over various time points in a clump-based or aggregate multi passage expansion.

Figure 10:
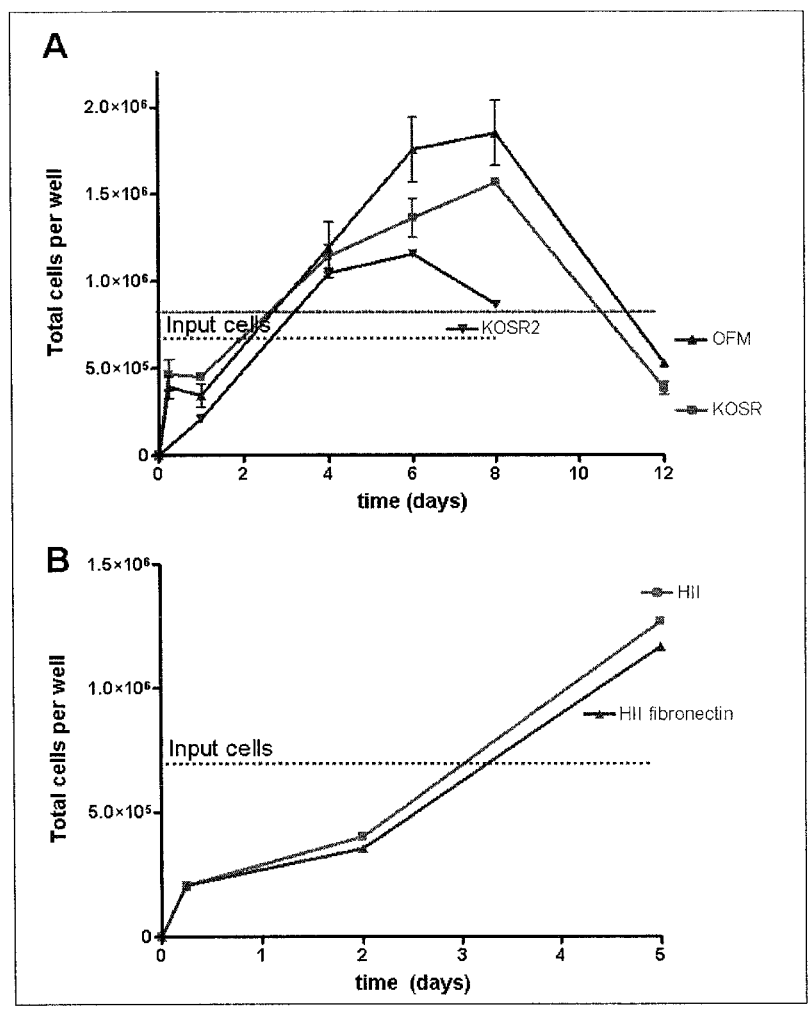

FIG. 10 shows the growth kinetics of ESI-017 on cationic amine tri-methylamine coated microcarriers over various time points in a clump-based or aggregate single passage expansion in fibroblast co-cultures (A) and in feeder free cultures (B).

Figure 11:
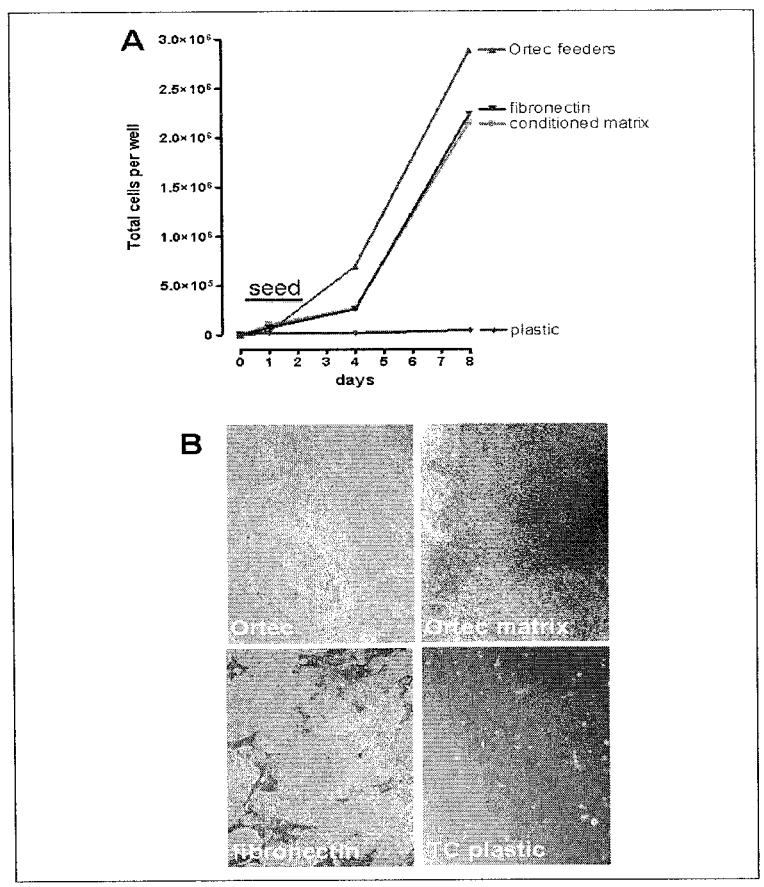
Figure 11:
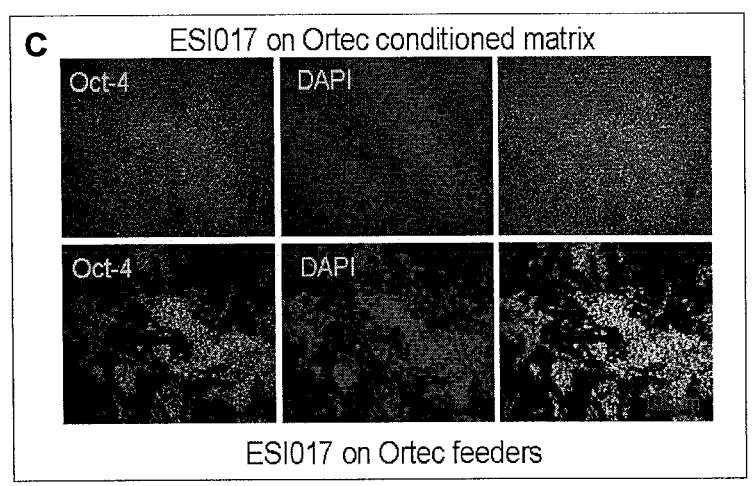

FIG. 11 shows the attachment and growth of single-cell suspension passage adapted ESI-017 cells on four different matrices, fibroblast feeders, fibronectin, conditioned fibroblast matrix or TC plastic. Cell count at various time points following dissociation of wells is shown in (A) and the photomicrographs of the morphology of the cells on various matrices at day 8 (B). Cells cultured long term under single cell passaging regimes retains the pluripotency markers, Oct-4 (panel 1) on fibroblast conditioned matrix or on fibroblast feeders (C). Green labeling represent specific markers of interest, blue staining represent DAPI (panel 2) in immunohistochemical analysis (C). The third panel (the two images on the right hand side of FIG. 11C) is a merge of the first 2 (i.e., Oct-4+DAPI).

Figure 12:
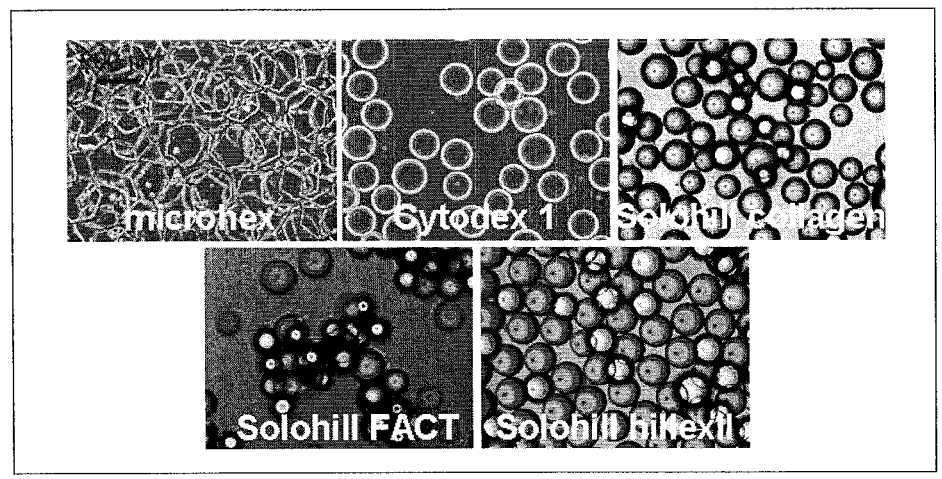
Figure 12:
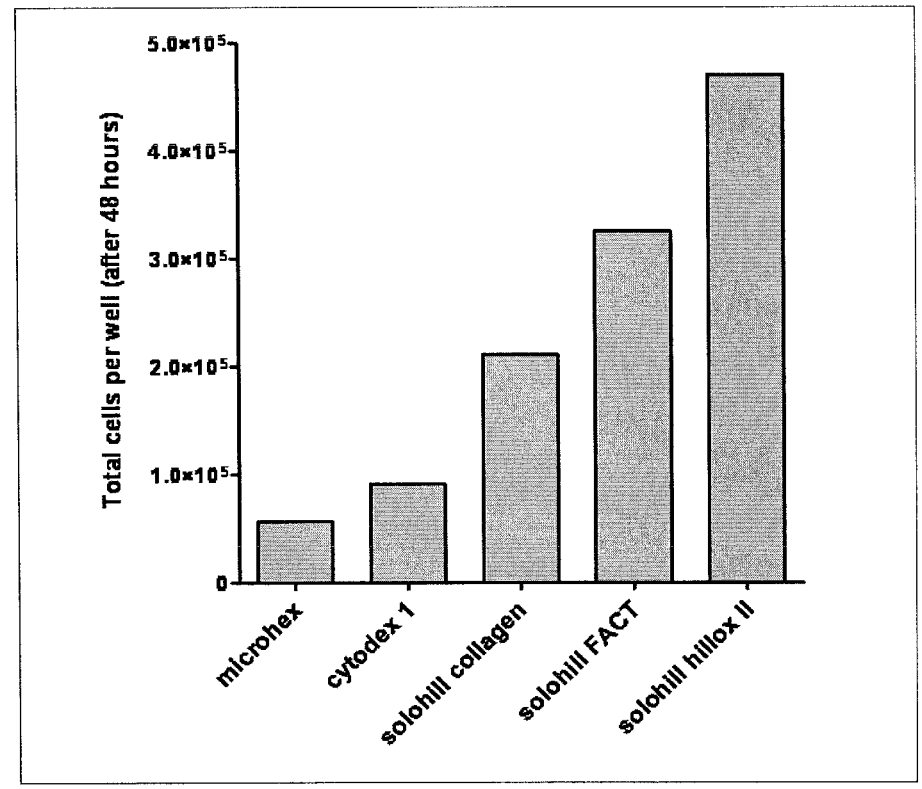

FIG. 12 represents single cell suspension of ESI-017 hES cells on different types of microcarrier beads. Photomicrographs of the morphology of single cell suspensions (A) and quantification of attached ESI-017 cell number (B) on different microcarrier beads

DETAILED DESCRIPTION OF THE INVENTION

In a first aspect, the present invention provides a method of promoting the attachment, survival and/or proliferation of a stem cell in culture, the method comprising culturing a stem cell on a positively-charged support surface.

Preferably, the method of the present invention provides an environment that is capable of supporting the attachment, survival and/or proliferation of stem cells, more preferably undifferentiated stem cells. In a further preferred embodiment of the present invention, the stem cell is a mammalian stem cell, more preferably an embryonic stem cell and most preferably a human embryonic stem cell.

The present inventors have found, surprisingly, that a support surface that is positively charged will promote the attachment and survival of a variety of stem cells, at least equivalent to standard culture surfaces using conventional conditions (e.g., incubation on conventional tissue culture polystyrene surfaces using commercial culture media, either with or without serum). It has also been found that a support surface that is positively charged molecule will inhibit the differentiation of the stem cells.

The present invention has the advantage that it provides a stem cell culture platform that allows the stem cell attachment process to be controlled by the positive charge on the support surface. It eliminates the need for non-specifically (i.e., randomly and arbitrarily) adsorbed serum proteins which form a layer on the culture substrate and also eliminates the need to use other uncharacterized or unpurified animal products, such as basement membrane matrix under the brand name Matrigel™ from Collaborative Biomedical Products.

Another advantage of the present invention is the ability to obviate the use of feeder cells, therefore eliminating or significantly reducing the potential contamination of the stem cell compositions though biohazardous agents, immunogenic or otherwise harmful products.

Support Surface

In a preferred embodiment, the positively-charged support surface is essentially free of other cell support factors, eliminating the need for using potential contaminants. Preferably, the positive charge is provided by the material from which the support surface is made. That is, the material(s) which make up the support surface may contribute to the positive charge of the surface.

Alternatively, the support surface of the present invention may comprise a solid, preferably polymeric, support to which a positively-charged molecule is bound.

A variety of articles may comprise the support surface of the present invention and suitable articles will be evident to those of skill in the art. Such articles include cell culture vessels, such as slides (e.g., tissue slides, microscope slides, etc.), plates (e.g., culture plates or multi-well plates, including micro plates), flasks (e.g., stationary or spinner flasks), bottles (e.g., roller bottles), bioreactors, and the like. Alternatively, the support surface may be part of a medical device, including, but not limited to, a scaffold or template for generating a two- or three-dimensional (3D) implant, tissue and/ or organ. Articles such as scaffolds or templates may be made of any suitable material, such as glass, plastic, foam or fiber meshes. Other suitable support surfaces include tubes, sutures, membranes, films, microparticles and microcarrier beads (preferably made of plastic).

The support surface for use with the present invention may be made of a variety of materials, including natural polymers, synthetic polymers and inorganic composites. Natural polymers include, for example, collagen- and glycosaminoglycan (GAG)-based materials. Synthetic polymers include, for example, poly(a-hydroxy acids) such as polylactic acid (PLA), polyglycolic acid (PGA) and copolymers thereof (PLGA), poly(ortho ester), polyurethanes, and hydrogels, such as polyhydroxyethylmethacrylate (poly-HEMA) or polyethylene oxide-polypropylene oxide copolymer. Hybrid materials, containing naturally derived and synthetic polymer materials, may also be used. Non-limiting examples of such materials are disclosed in Chen et al. (*Advanced Materials* 12:455-457, 2000). Inorganic composites include, for example, calcium phosphate ceramics, bioglasses and bioactive glass-ceramics, in particular composites combining calcium hydroxyapatite and silicon stabilized tricalcium phosphate. Among preferred support surfaces are polystyrene, polypropylene, polyethylene, polyethylene terephthalate, polytri- or tetra-fluoroethylene, polyhexafluoropropylene, polyvinyl chloride, polyvinylidine fluoride, polylactide, cellulose, glass, or a ceramic. In a preferred embodiment, the support surface is a polystyrene tissue culture dish or multi-well plate. The support surface may be microcarrier bead surface.

Positively-Charged Molecule

As used herein, the term "positively-charged molecule", refers to a molecule that increases the positive charge density of the support surface. The positively charged molecule may be added to the support surface to increase the positive charge on that surface. Suitable positively-charged molecules generally provide an optimal combination of such properties as solubility, charge density, film-forming ability, and hydrophilicity. In a preferred embodiment, the positively-charged molecule for use in the methods of the present invention is a cationic compound including, but not limited to, trimethylammonium (the positively charged cationic of trimethylamine)(for the purpose of the present invention trimethylammonium will also be referred to as cationic trimethylamine), polycationic polymers with amino groups (such as polyetherimide, poly-L-lysine, poly-D-lysine (PDL), poly-L-ornithine (PLO), poly-D-ornithine (PDO), poly(vinylamine) (PVA), poly(allylamine) (PAA)), or combinations thereof.

The positively charged molecules may be on a microcarrier bead surface. The microcarriers may include but may not be limited to Cytodex 1, Cytodex 3, Microhex, Cultisphere, Solohill collagen, Solohill FACT, Solohill hillex II, Solohill pronect or Solohill plastic+. In particular the microcarrier may be Hillex II microcarrier (a cationic trimethylamine support)(SoloHill Engineering, inc.). For the purpose of the present invention the terms cationic trimethylamine and Hillex II are used interchangeably.

Examples of other suitable molecules are polymers that possess positively charged groups together with other functionalities that enable the polymer to be stably coated (e.g., covalently) onto at least a portion of the support surface. Examples of positively charged groups include primary, secondary, and tertiary amines as well as quaternary ammonium salts. Such charged groups can be incorporated into a polymer in the form of monomers such as N-(3-aminopropyl) methacrylamide (APMA), N-(3-dimethylaminopropyl) methacrylamide, methacrylamidopropyl trimethylammonium chloride, aminostyrene, vinyl pyridine, ornithine, and lysine. Other groups suitable for the incorporation of positive charge into a molecule include amidines, guanidines, hydrazines, and phosphonium salts.

Preferred charged polymers are synthetic. The term "synthetic", as used herein, means either polymerized from monomers and/or oligomers, at least some of which include the positively charge group or groups of choice, and/or prepared by the chemical modification of naturally-occurring polymeric backbones. The synthetic polymers can be prepared by the use of addition- or condensation-type polymerization mechanisms. Addition-type polymers include, but are not limited to, acrylics such as those polymerized from methyl acrylate, methyl methacrylate, hydroxyethyl acrylate, hydroxyethyl methacrylate, acrylic acid, methacrylic acid, acrylamide, and methacrylamide, as well as vinyls such as styrene, vinyl chloride, vinyl pyrrolidone, vinyl acetate, ethylene, propylene, and tetrafluoroethylene. Examples of condensation type polymers include, but are not limited to, nylons such as polycaprolactam, polylauryl lactam, polyhexamethylene adipamide, and polyhexamethylene dodecanediamide, as well as polyurethanes, polycarbonates, and polyimides.

Examples of other synthetic polymers within the scope of the present invention include derivatives of cellulose, including, but not limited to, diethyl aminoethyl cellulose, carboxy methyl cellulose, aminoethyl cellulose, and chitosan.

The positively-charged molecule is generally used at a density that is sufficient to support the attachment of the stem cell to the support surface. The appropriate density can be determined by those skilled in the art and will depend upon such factors as the configuration of support surface used, the material from which the supporting surface is made, and the type of stem cell that is to be attached to the support surface.

A sufficient density of positively-charged molecule should be carried by the supporting surface to provide the support surface with an ion-exchange capacity at a physiologic pH to promote initial stem cell attachment, survival and/or proliferation. Ion-exchange capacity is a quantitative measurement of the amount of a negatively-charged reagent that can bind to the bioreactor surface, per unit area. The rate of cell attachment to a bioreactor surface is reported to correlate more closely with ion-exchange capacity than with charge density (Himes and Hu, 1987).

The exchange capacity of a DEAE-dextran bead microcarrier (as an example of a suitable, support surface) can be determined by titration of bound DEAE-HCl molecules as described by Levine et al, (Levine et al 1979), the disclosure of which is incorporated herein by reference. DEAE-dextran microcarriers are typically washed with 0.1 molar HCl (0.5 L/g dry dextran beads) to allow for the saturation of the exchange sites with chloride ions. In order to remove unbound chloride ions, the beads are rinsed with dilute HCl (10-4 M, 0.8 L/g dry dextran beads). The beads are then washed with 10% (w/w) sodium sulfate (75 mL/g dry dextran beads) and the filtrate collected. The last wash displaces the bound chloride ions with sulfate ions. 100 mL of the filtrate is titrated with 1.0 molar silver nitrate in the presence of potassium chromate as an indicator (1 mL 5% w/w solution).

Preferably, the positively-charged molecule is covalently or non-covalently bound to the support surface. It is preferably covalently bound. In another embodiment, the positively-charged molecule can each be covalently bound to the support surface through a linking group. Preferably, the positively-charged molecule is uniformly and homogeneously distributed on the support surface. In a preferred embodiment, the positively-charged molecule forms a homogeneous blend on the support surface, and is located on the support surface in such a manner that it is presented (i.e., physically accessible) to a stem cell to be affixed to the support surface. The support surface of the stem cell culture system (e.g., the cell-contacting surface of a bioreactor of the present invention), bears a density of positively-charged molecules that is sufficient to promote and stabilize cell attachment to the surface.

Whilst it is most preferred that the positively-charged support surface is essentially free of any other extraneous material (such as extracellular matrix proteins and feeder cells), in a preferred embodiment, the positively-charged support surface of the present invention may also be supplemented with other factors that promote the attachment, survival and/or proliferation of stem cells, including (but not limited to) extracellular matrix proteins such as elastin, fibronectin, vitronectin, tenascin, laminin, entactin, aggrecan and decorin, or a biologically active fragment or variant thereof, as well as collagen, such as collagen I, collagen III, collagen IV or collagen VI, or a biologically active fragment or variant thereof, or combinations thereof. Elastin, fibronectin, vitronectin, collagen I, collagen III, and collagen IV are most preferred. Preferably, the extracellular matrix proteins are synthetically generated.

A positively-charged support surface is said to be essentially free of extraneous material such as extracellular matrix proteins if less than about 5% of the surface area comprises the extraneous material. Positively-charged support surfaces containing less than 1%, 0.2%, 0.05%, or 0.01% extraneous material (expressed as % of surface area of the support surface) are increasingly more preferred.

Stem Cells

Whilst any type of stem cell may be used in accordance with the methods of the present invention, in a preferred embodiment, the stem cell is a human embryonic stem cell (hES cell). The scope of the term covers pluripotent stem cells that are derived from a human embryo at the blastocyst stage, or before substantial differentiation of the cells into the three germ layers. Those skilled in the art will appreciate that except where explicitly required otherwise, the term includes primary tissue and established lines that bear phenotypic characteristics of stem cells, and derivatives of such lines that still have the capacity of producing progeny of each of the three germ layers. In particular, any hES cell line included in the NIH Registry may be used; for example, hES cell lines from ES Cell International (ESI). More in particular, the cells may be hES-2 cells. Other hES cells from ESI, like ES017 cells may also be used.

Stem cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated stem cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighbouring cells that are differentiated. Nevertheless, the undifferentiated colonies persist when the population is cultured or passaged under appropriate conditions, and individual undifferentiated cells constitute a substantial proportion of the cell population.

Cultures that are substantially undifferentiated contain at least 20% undifferentiated stem cells, and may contain at least 40%, 60%, or 80% in order of increasing preference (in terms percentage of cells with the same genotype that are undifferentiated).

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

"Feeder cells" or "feeders" are terms used to describe cells of one type that are co cultured with cells of another type, to provide an environment in which the cells of the second type can grow. The feeder cells may be human or non human feeder cells. In particular the feeder cells may be mouse embryonic feeder cells. More in particular the feeder cells may be human foreskin fibroblasts.

Stem cell populations are said to be essentially free of feeder cells if the cells have been grown through at least one round after splitting in which fresh feeder cells are not added to support the growth of stem cells. A feeder-free culture will contain less than about 5% feeder cells. Compositions containing less than 1%, 0.2%, 0.05%, or 0.01% feeder cells (expressed as % of total cells in the culture) are increasingly more preferred.

Environment for Culturing Stem Cells

In accordance with the methods of the present invention, the stem cells are cultured in an environment that includes a nutrient medium or culture medium that is capable of supporting the attachment, survival and/or proliferation of a stem cell in vitro or ex vivo. A person skilled in the art of culturing stem cells would be familiar with techniques for culturing these cells, for instance, as evidenced in U.S. Pat. No. 6,875,607, the entire contents of which are incorporated herein by reference.

The terms "nutrient medium", "cell culture medium," "culture medium" and "medium formulation" and the like refer to a nutritive solution for culturing or growing cells, preferably stem cells (whether differentiated or undifferentiated) that contain nutrients that are capable of supporting the survival and/or proliferation of the cells, and/or their attachment to the positively-charged support surface. The nutrient medium may contain any of the following in an appropriate combination: isotonic saline, buffer, amino acids, serum or serum replacement, and other exogenously added factors.

The phrase "capable of supporting" is used herein to define an environment comprising at least one (preferably soluble) factor or reagent that provides a cell cultured therein with an environment that will (i) allow the cell to become attached to the positively charged support surface and/or (ii) allow the cell to survive within that environment for a required period of time and/or (iii) provide a stimulus for the proliferation of that cell. Conversely, the phrase "capable of supporting" can also be used herein to define an environment that is absent a (preferably soluble) factor or reagent that would normally (i) inhibit the attachment of a cell cultured therein to the positively-charged support surface and/or (ii) inhibit cell survival, such as through apoptotic or necrotic mechanisms and/or (iii) inhibit the proliferation of the cell in that environment.

Thus, the term "capable", as used herein to describe culture conditions, preferably denotes conditions that result in a measurable amount of cell attachment, survival and/or proliferation. Effective conditions can be readily determined and/or optimized by a skilled worker using conventional methods. Among the factors to be varied include, for example, the seeding density, the vessel, the culture medium, the temperature, the $O_2/CO_2$ concentrations, and the like.

Thus, the skilled person will know that any of a variety of culture medium capable of supporting the attachment, survival and/or proliferation of stem cells may be used in conjunction with the methods of the present invention. Commercially available culture medium, such as DMEM, F12, aMEM, Hepatocyte Defined Medium under the brand name Hepatostim™ from BD Biosciences (San Jose, Calif.), RPMI, or combinations thereof, may be used, either in the presence or absence or serum. Suitable sera include calf serum, fetal calf serum, horse serum, or the like. The skilled addressee would also know that a serum supplement could be used in place of serum in the culture media.

Preferably, the culture media is a human fibroblast conditioned media comprising a basal medium optimized for growth of undifferentiated embryonic and induced pluripotent stem cells under the brand name Knockout™ D-MEM from Gibco/BRL, supplemented with 20% Invitrogen Serum-Replacement™, 25 ng/mL bFGF, 0.1 mM b-mecaptoethanol, 1% NEAA, 2 mM L-glutamine, 25 U/mL 15 penicillin and 25 mg/mL streptomycin.

A "conditioned medium" is prepared by culturing a first population of cells in a medium, and then harvesting the medium. The conditioned medium (along with anything secreted into the medium by the cells) may then be used to support the growth of a second population of cells. Where a particular ingredient or factor is described as having been added to the medium, what is meant is that the factor (or a cell or particle engineered to secrete the factor) has been mixed into the medium by deliberate manipulation.

Thus, it is also an aspect of the present invention to provide a conditioned medium derived by culturing a stem cell on a positively-charged support surface in accordance with the methods of the invention herein described.

By contrast, "fresh medium" is a medium that has not been purposely conditioned by culturing with a different cell type before being used with the cell type it is ultimately designed to support. Otherwise, no limitations are intended as to its manner of preparation, storage, or use. It is added fresh (by exchange or infusion) into the ultimate culture, where it may be consumed or otherwise processed by the cell types that are present.

By "cell culture" is meant cells or tissues that are maintained, cultured or grown in an artificial, in vitro or ex vivo environment.

As used herein, reference to stem cell "attachment" means binding of the stem cell to the support surface such that the stem cell is not eluted by conventional washing or handling procedures. By stem cell "survival," particularly in regards to an undifferentiated stem cell, is meant sustained viability.

The terms "proliferation" and "propagation" are used interchangeably herein to denote an increase in the number of cells. The term "expanded" is also intended to mean that the resultant cell population is derived from ex vivo culture of stem cells, where the outgoing (cultured) number of cells exceeds the ingoing (non-cultured) number of cells. The term "expanded" is not to be construed or limited by any mechanism or theory of cellular origin and may comprise cells that originate de novo in culture.

The stem cell may be brought into contact with the support surface by any suitable means. For example, a stem cell in a culture medium may be poured, pipetted or dispensed into a culture vessel comprising the support surface, or a medical device or scaffold comprising the support surface may be submerged in culture medium in which the stem cell is suspended.

In the accordance with the methods of the present invention, a stem cell is preferably cultured on a positively-charged support surface under conditions capable of supporting the attachment, survival and/or proliferation of the stem cell.

Screening Assays

Another aspect of the invention is a method for identifying a test sample containing an agent or factor that modulates (e.g., stimulates, inhibits, potentiates, etc.) the attachment, survival, proliferation and/or differentiation of a stem cell in culture, comprising (a) contacting the stem cell (preferably in a culture medium lacking serum) with (i) a positively-charged support surface and (ii) a test sample suspected of including the agent or factor, and (b) measuring the attachment, survival, proliferation and/or differentiation of the stem cell compared to the attachment, survival, proliferation and/or differentiation of a similar stem cell in a culture in the absence of the test sample.

It is expected that (i) increased attachment, survival, proliferation and/or differentiation in the presence of the test sample indicates the presence in the test sample of a factor that stimulates the attachment, survival, proliferation and/or differentiation of the stem cell, and (ii) decreased attachment, survival, proliferation and/or differentiation in the presence of the test sample indicates the presence in the sample of a factor that inhibits the attachment, survival, proliferation and/or differentiation of the stem cell. The comparison can be made to a stem cell to which the test sample has not been added, which is grown in parallel with the experimental sample; or the comparison can be made to a reference database. The test sample may be a pure compound whose effects are unknown, or a composition whose contents and effects are unknown.

One of skill in the art will recognize a variety of types of agents or factors that can be tested in this method. For example, the method can be used to test putative drugs (e.g., proteins, peptides, small molecules, nucleic acids, such as antisense molecules, ribozymes or RNAi, or the like) that affect an activity of the stem cell of interest (e.g., an intercellular signalling cascade, a metabolic pathway, etc.). In addition to drug screening, drug discovery, and the identification of potential drug targets, the method can be used to determine if a potential factor or agent is toxic to the stem cell and has a measurable detrimental effect, induces unregulated proliferation (oncogenic transformation), etc.

Among the types of factors or agents that can be tested are proliferation factors, such as angiopoietin 2, BMP2, BMP4, erythropoietin, aFGF, bFGF, HGF, insulin, noggin, PDGF, TNF, VEGF, stem cell factors, GDF6, CSF, FH3/F2, TGFb, or the like. Alternatively, one can test small molecules generated by conventional combinatorial chemistry, or peptide libraries. Other types of factors or agents will be evident to the skilled worker.

Among the types of factors or agents that can be tested are differentiation factors that can induce the differentiation of a stem cell to a required lineage. The state of differentiation of a stem cell culture can be assessed most easily by judging the morphological characteristics of the cells. Undifferentiated stem cells generally have a characteristic morphology; that is, small and compact cells with clearly defined cell borders, a morphology which can be easily seen by examination of a stem cell culture under a microscope. By contrast, cells which have differentiated appear larger and more diffuse, with indistinct borders. While some differentiated cells can, and normally do, appear at the margin of colonies of undifferentiated cells, the optimal stem cell culture is one that proliferates in the culture vessel with only minimal numbers of cells at the periphery of the culture appearing to be differentiated. With experience, one can judge the status of differentiation and health of human ES cell cultures visually with good accuracy. A biochemical marker that is used to track the status of ES cells as undifferentiated is the presence of the transcription factor Oct4, which has come to be regarded as the most reliable marker of undifferentiated status of ES cells, and which is one of the first markers lost as undifferentiated cells begin to differentiate.

Any of the methods of the invention can be adapted to high throughput procedures, as one or more of the processes may be achieved robotically.

Kits

Another aspect of the invention is a kit useful for promoting the attachment, survival, proliferation of stem cells, comprising (a) a positively-charged support surface and (b) one or more components or reagents suitable for culturing stem cells (e.g., a culture vessel, an appropriate culture medium and/or factor(s) that enhance stem cell proliferation in vitro, etc.).

Another kit of the present invention useful for identifying a factor or agent that modulates the attachment, survival, proliferation and or differentiation of a stem cell in culture, comprises a positively-charged support surface and at least one component or reagent capable of supporting stem cell attachment, survival, proliferation and/or differentiation in the culture. The component or reagent may include a culture vessel, an appropriate culture medium, factor(s) that enhance stem cell attachment, survival, proliferation and or differentiation, and/or one or more reagents, such as those described herein, that can be used to measure stem cell attachment, survival, proliferation and or differentiation.

Such kits have many uses, which will be evident to the skilled worker. For example, they can be used to propagate stem cells of interest, particularly for use in cell therapy, etc., to characterize agents, such as putative therapeutic agents and to identify agents that play a role in a stem cell function of interest, etc. Such kits could be of commercial use, e.g., in high-throughput drug studies.

Stem Cell Differentiation and Tissue Engineering

In yet another aspect of the present invention, there is provided a method of using stem cells that have been derived from the methods of the present invention for cell transplantation or to engineer tissue to treat various disorders or diseases, including (but not limited to) those of the cardiovascular system, muscle, ligament, bone, tendon, cartilage, nervous system, blood, immune system, liver, or pancreas. The need for replacement tissues and/or organs, in combination with the shortage of suitable donors, has been a strong incentive for the development and production of tissue engineered implants that can take over the function of missing or injured body parts. An advantage of these "engineered" replacement tissues and organs is that they may circumvent many of the hazards and problems associated with donor tissues and organs, and at lower cost. Today, tissue engineering applications cover virtually every human tissue, including skin, eyes, liver, pancreas, blood vessels, ligaments, cartilage, bone, muscle and parts of the nervous system.

In one embodiment, the method of tissue engineering (TE) involves the derivation of undifferentiated stem cells by a method according to the present invention, and the seeding of the undifferentiated stem cells onto a biological or artificial scaffold in vitro prior to transplantation of the seeded scaffold into a specific location of the recipient. Prior to the implantation of the seeded scaffold in vivo, the seeded cells can be induced by: specific bioactive molecules such as growth factors, by ex vivo gene transfer or by other physical factors to form the required tissue in vitro. Alternatively, the scaffold comprising the growth factors may be combined with the cells in vivo. For example, bone-marrow derived mesenchymal stem cells can be expanded, differentiated to bone-forming osteoblasts and subsequently seeded on a biodegradable scaffold. The scaffold is thus osteoconductive, in that it provides a path for the growing bone tissue. The in vitro prepared and loaded scaffold is then implanted in a bone defect and while the seeded cells are induced to form new bone material, the scaffold itself is degraded. A further example is that of human articular cartilage repair using the patient's own autologous chondrocytes retrieved at arthroscopy. The chondrocytes are expanded in vitro before being reimplanted into full-thickness articular cartilage defects covered with a sutured and fibrin-glued periosteal patch. Of course, tissues or organs may also be produced completely in vitro and transplanted as ready replacement materials.

In a preferred embodiment, the stem cells derived from the methods of the present invention are differentiated towards a given lineage prior to seeding onto the scaffold. For example, stem cells derived from bone marrow, including mesenchymal stem cells (MSC) typically form connective tissues such as bone, cartilage, tendon, ligament, bone marrow stroma, mucous tissue, fat and muscle. These progenitor cells may be induced by specific bioactive molecules to mature into a required cell type. MSCs may, for instance, be induced to form osteoblasts by using dexamethasone. Once matured, the cells are then seeded onto the scaffold.

Although not exclusively, TE techniques generally involve the use of a temporary biodegradable scaffold that serves as 3D template for initial cell attachment and subsequent tissue formation. The ability of the scaffold to be metabolized by the body allows it to be gradually replaced by new cells to form functional tissues.

The term "scaffold", as used herein, is defined as a biological or artificial tissue engineering carrier matrix for tissue-regenerating cells. A scaffold may be a biocompatible scaffold, a bioactive scaffold and/or a biodegradable scaffold, preferably a biodegradable scaffold. The term scaffold is not limited to any form and may for instance be in the form of a more or less rigid object, or in the form of an amorphous material. Suitable scaffolds are described in U.S. patent application Ser. No. 11/298,208, the entire contents of which are incorporated herein by reference.

As used herein, the term "tissue" is defined as a coordinated assemblage of one or more types of differentiated cells including, where applicable, their connective tissue and/or mineral matrix, such as, but not limited to, bone tissue, skin tissue, eye tissue, liver tissue, pancreas tissue, blood vessel tissue, ligament tissue, cartilage tissue, muscle tissue and nervous system tissue.

The term "implanting", as used herein, is used in its art-recognised meaning and is defined as introducing into a body by surgical or non-surgical methods a biological or artificial material, in particular a scaffold material.

The terms "seeded" and "seeding", as used herein, relate to a partially or essentially completely loaded scaffold, respectively to the process of loading or inoculating a scaffold with tissue-regenerating cells. Seeding may occur onto and/or into a scaffold matrix material. Preferably, seeding is performed by injection of tissue-regenerating cells onto and/or into the scaffold, or by injection of tissue-regenerating cells in peripheral blood vessels allowing "homing" of the cells to the implant site and into and/or onto the scaffold.

The term "tissue-regenerating cells", is used herein to indicate one or more types of cells derived from the method of the present invention that may be seeded onto and/or into a scaffold and that are capable of the formation of a coordinated assemblage of one or more types of differentiated cells, optionally including a connective tissue and/or mineral matrix, thereby forming a tissue.

Cell Compositions

In another aspect, the present invention provides a cell composition comprising an expanded population of undifferentiated or substantially undifferentiated stem cells derived from the method of the present invention, as herein described.

In yet another aspect, the present invention provides a cell composition comprising an expanded population of differentiated or substantially differentiated stem cells that is derived by contacting the expanded population of undifferentiated or substantially undifferentiated stem cells to an agent that is capable of promoting the differentiation of a stem cell towards a given lineage.

A "composition", as used herein, preferably refers to an in vitro preparation of dispersed cells. Preferably, a composition of "substantially undifferentiated" stem cells consists of a preparation of at least 10% and more preferably 50% of undifferentiated stem cells derived from culturing a stem cell in accordance with the methods of the present invention.

Cell Culture System

In another aspect, the present invention provides a cell culture system comprising stems cells cultured on a positively-charged support surface in accordance with the methods of the invention herein described.

According to another aspect, there is provided an aggregate cell culture cultured on a positively-charged support surface. The aggregate (also indicated as "clump") cull culture may be prepared according to any aspect of the method of the present invention. Aggregate means two or more cells clustered together. An example of preparation of aggregate (or clump) cell culture is given in Example 8(A).

According to another aspect, there is provided a single cell culture cultured on a positively-charged support surface. The single cell culture may be prepared according to any aspect of the method of the present invention. An example of preparation of single-cell culture is given in Example 8(B).

Throughout the description and claims of this specification the word "comprise", and variations of the word such as "comprising" and "comprises", are not intended to exclude other additives or components or integers or steps.

"Medicament" and "Use"

In yet another aspect. There is also provided the use of a cell composition comprising an expanded population of undifferentiated or substantially undifferentiated stem cells derived from a method of promoting the attachment, survival and/or proliferation of a stem cell in culture comprising culturing at least one stem cell on a positively-charged support surface according to the present invention, or the use of at least one cell derived from the above cell composition, or the use of at least one biological tissue engineered by a method comprising the step of directing the differentiation of the above cell composition, for the preparation of a medicament for treating and/or preventing at least one disorder or disease. There is also provided at least one cell derived from the above cell composition, the above cell composition, or at least one biological tissue engineered by the above method, for use in treating and/or preventing at least one disorder or disease.

It would also be well appreciated by one skilled in the art that the methods of treatment hereinbefore described could be used in any number of combinations with each other, or with other treatment regimes currently employed in the art.

Examples of the procedures used in the present invention will now be more fully described. It should be understood, however, that the following description is illustrative only and should not be taken in any way as a restriction on the generality of the invention described above.

EXAMPLES

Example 1

Morphological Analysis of hES Cell Culture following Propagation on Cationic Amine Tri-Methylamine Coated Microcarriers All microcarrier experiments were performed using Hillex II cationic tri-methylamine coated microcarriers (SoloHill Engineering, Inc.). Human ESC, hES-2 (http://stemcells.nih.gov/research/registry/esci.asp) were propagated on microcarriers in flat bed culture plates (see panel A of FIG. 1) or in bulb stirred culture vessels (see panels B and C of FIG. 1). Cells were passaged using Collagenase IV disaggregation and collected for subsequent seeding to fresh beads. Cultures were maintained in human fibroblast feeder conditioned media comprising Invitrogen KO-DMEM supplemented with 25 ng/mL bFGF, 20% Invitrogen KO-SR, 0.1 mM β-mercaptoethanol, 1% NEAA, 2 mM L-glutamine, 25 U/mL penicillin, and 25 μg/mL streptomycin. Following conditioning, media was further supplemented with additional 25 ng/mL bFGF. The cultures comprised small uniform clumps of cell-coated beads in suspension. hES cells formed high density colonies with healthy undifferentiated (non-cystic) morphology. Data confirms hES cell proliferation with culture through extended passage supporting the efficiency of the culture method.

Example 2

Immunohistochemical Analysis of hES Cells following Propagation on Cationic Amine Tri-Nethylamine Coated Microcarriers hES-2 hES cells were propagated for 7 days on microcarriers in flat bed culture plates. Cultures were maintained in human fibroblast feeder conditioned media comprising Invitrogen KO-DMEM supplemented with 25 ng/mL bFGF, 20% Invitrogen KO-SR, 0.1 mM β-mercaptoethanol, 1% NEAA, 2 mM L-glutamine, 25 U/mL penicillin, and 25 25 μg/mL streptomycin. For immunophenotyping, cells were harvested from microcarriers using Collagenase IV disaggregation, cytospun to glass slides and fixed for immunohistochemistry. Cells were fixed with 4% paraformaldehyde and stained for Oct-4 (i; Santa Cruz Biotechnology), TRA 1-81 (ii; Chemicon) or SSEA-1 (iii; Chemicon) (FIG. 2A). The data confirms the maintenance of undifferentiated hES cells, thus verifying the efficacy of chosen method.

Example 3

Flow Cytometric Analysis of hES Cells following Propagation on Cationic Amine Tri-Methylamine Coated Microcarriers hES-2 hES cells were propagated on microcarriers in bulb stirred culture vessels. Cells were passaged using Collagenase IV disaggregation and collected for subsequent seeding to fresh beads. Cultures were maintained in human fibroblast feeder conditioned media comprising Invitrogen KO-DMEM supplemented with 25 ng/mL bFGF, 20% Invitrogen KO-SR, 0.1 mM β-mercaptoethanol, 1% NEM, 2 mM glutamine, 25 U/mL penicillin, and 25 μg/mL streptomycin. Following conditioning, media was further supplemented with additional 25 ng/mL bFGF. Cells were fixed with 4% paraformaldehyde and stained for Oct-4, TRA 1-81 (Chemicon) and analysed by flow cytometry. Relative to negative controls (i.e. isotype antibody labelling; see FIG. 2B, left-hand pink open plots), cells sustained high level expression (see FIG. 2B, right-hand blue open plots) of both markers, indicating undifferentiated hES cells. Clearly, this data confirm hES cell maintenance with undifferentiated (immunopositive) cell growth, supporting the efficacy of culture method. Control cultures comprised traditional plate based hES-2 on human fibroblast feeders.

Example 4 hES Cell Expansion by Propagation on Cationic Amine Tri-Methylamine coated Microcarriers in Bulb Stirred Culture Vessels Human ESC, hES-2, were propagated on microcarriers in bulb stirred culture vessels over 5 weeks through 5 passages. Cells were passaged using Collagenase IV disaggregation and collected for subsequent seeding to fresh beads. Cultures were maintained in human fibroblast feeder conditioned media comprising Invitrogen KO-DMEM supplemented with 25 ng/mL bFGF, 20% Invitrogen KO-SR, 0.1 mM β-mercaptoethanol, 1% NEM, 2 mM L-glutamine, 25 U/mL penicillin, and 25 μg/mL streptomycin. Following conditioning, media was further supplemented with additional 25 ng/mL bFGF. Viable cell number was determined during each passage by Trypan blue exclusion method. The data presented in FIG. 3A represent the combined cell counts of two culture vessels.

Example 5 hES Cell Expansion by Propagation on Cationic Amine Tri-Methylamine Coated Microcarriers in Bulb-Stirred Culture Vessels hES-2 hES cells were propagated on microcarriers in bulb stirred culture vessels over 4 weeks through 4 passages. Human ESCs were passaged using Collagenase IV disaggregation, strained and collected for subsequent seeding to fresh beads. Cultures were maintained in human fibroblast feeder conditioned media comprising Invitrogen KO-DMEM supplemented with 25 ng/mL bFGF, 20% Invitrogen KO-SR, 0.1 mM β-mercaptoethanol, 1% NEM, 2 mM L-glutamine, 25 U/mL penicillin, and 25 μg/mL streptomycin. Following conditioning, media was further supplemented with additional 25 ng/mL bFGF. Viable cell number was determined by Trypan blue exclusion method. The data presented in FIG. 3B represent the mean of duplicate cell counts of a single culture vessel. Viable cell number represented 86.5% of total cells harvested.

Example 6 hES Cell Expansion by Propagation on Cytodex 1 Microcarriers Consisting of a Cross Linked Dextran Matrix Substituted with Cationic N,Ndiethylaminoethyl Groups hES-2 hES cells were propagated for 11 days on positively charged Cytodex 1 microcarrier beads in flat bed culture plates with human fibroblast feeder conditioned media comprising Invitrogen KO-DMEM supplemented with 25 ng/mL bFGF, 20% Invitrogen KO-SR, 0.1 mM β-mercaptoethanol, 1% NEM, 2 mM L-glutamine, 25 U/mL penicillin, and 10 25 µg/mL streptomycin. Following conditioning, media was further supplemented with additional 25 ng/mL bFGF. Cells were harvested for counting by collagenase IV disaggregation. Viable cell number was determined by Trypan blue exclusion method. The data presented in FIG. 3C represent cell counts of a single culture vessel. The profiling indicates hES cell supportability with expansion from $9.8 \times 10^4$ to $5.0 \times 10^5$ cells.

Example 7

Culture of Human Foreskin Fibroblasts on Tri-Methylamine Microcarriers: Microcarrier Cultures In examples 7 and 8, ESI hES cells ESI-017 were used. However, other hES cells, like ESI hES-2 may also be used.

Prior to inoculation, 400 mg microcarrier beads were pre-cultured for at least 1 hour in 40 ml of fibroblast feeder medium (10 mg/ml). For inoculation, human fibroblasts were either directly thawed into the culture bottle, or seeded from the fibroblast cells growing in T175 flasks. In either case, cells were inoculated at $5 \times 10^6$ cells per bottle. Attachment of the cells occurred under static (no spinning) conditions overnight, with occasional agitation of the bottle approximately every hour. The next morning, the medium was topped up to a final 80 ml volume, and the bottles were transferred to a magnetic stirring platform and stirred at a rate of 40 revolutions per minute. All samples were collected in duplicate, by agitating the bottle, and collecting 2 separate 1 ml aliquots of medium and beads (FIG. 4). Depletion of free cells in the culture as the cells adhere to microcarriers occurred with first order kinetics independent of the starting cell concentration (FIG. 4A). The attachment of the cells followed the first order kinetics according to the equation i) $dC_f/dt = kC_f$ and ii) $\ln C_{fo} - \ln C_f = kt$ (FIG. 4B) wherein a plot of ($\ln C_{fo} - \ln C_f$) versus time will give a linear line with a slope equal to attachment coefficient. The growth of the fibroblasts over 7 days showed standard growth kinetics with a short lag phase, an exponential pahse and a pleateau (FIG. 4C). Morphological analysis of the cells showed a rapid attachment within several hours followed by flatter adhesion at 2 days. Over time small clusters appeared as the microcarriers and the cells clump together (FIG. 4D). Passage 7 (P7) human fibroblasts (5 million) were thawed directly into 80 ml of medium containing 400 mg hillex II microcarrier beads for multi-passage expansion and the expansion during each individual passage is shown in FIG. 4E.

P7 human fibroblasts were then expanded for 3 passages (thus P9 final), harvested, irradiated, and frozen in aliquots for storage. The cells were then thawed on demand as feeders for ESI-017 co-cultures (FIG. 5A). Alternatively, ESI hES-2 may be used in place of ESI-017. In this manner, ESI-017 cells were cultured for at least 5 passages on the microcarrier-expanded fibroblast cells and analysed for pluripotency markers by Oct-4 and Tra 1-60 by flow cytometry (FIG. 5B) or for markers Oct-4, Tra1-60 and SSEA by immunohistochemistry (FIG. 5C). In addition to co culture support, feeder fibroblasts could also condition culture medium for support of feeder free growth of hES cell as shown in FIG. 6. Human fibroblasts were expanded for 3 passages on microcarrier beads (seeded at 5 million cells onto 400 mg beads). After confluence for the last passage, the medium was replaced with hES cell culture medium (20% KOSR medium with 1×L-glutamine—100 ml per bottle) for overnight conditioning. This medium was then used for feeder-free hES cell culture medium (FIG. 6A). The ESI-017 cells were cultured in feeder-free conditions for at least 5 passages with conditioned medium generated from flat-bed human fibroblasts (flask CM) or from microcarrier-expanded human fibroblasts (microcarrier CM). The cells were then harvested and assessed for pluripotency marker expression by flow cytometry (FIG. 6B) or by immunohistochemistry (FIG. 6C). Regardless of the source of conditioned medium, the cells showed a high expression of both Oct4 and Tra1-60 indicating that CM produced by microcarrier-expanded human fibroblasts can support pluripotent hES cell growth.

Example 8

Culture of hES Cells, ESI-017 on Tri-Methylamine Microcarriers

A) Aggregate or Clump Based Cultures.

Aggregate or clump of cells refer to two or more cells clustered together. Initially, tri-methylamine microcarriers, Hillex II were pre-equilibrated in hES cell medium. For single passage attachment and growth assays, the density of microcarriers in 6-well ultra low plates was 50 mg/ml, 2 ml per well. Multi-passage experiments were performed in internal propeller spinner flasks, which contained 15 mg microcarriers per ml, 80 ml total volume. Unless specified, human fibroblast-conditioned hES cell medium were used. To prepare, a confluent T225 flask of fibroblasts were given hES cell medium during the medium change. The medium was conditioned for 24 hours before being collected and stored. Alternatively, confluent human fibroblast microcarrier cultures were used to condition hES cell medium.

The hES cells, ESI-017 used for all microcarrier cultures were obtained from cultures grown on mitotically inactive human foreskin fibroblasts plated at a density of $3 \times 10^5$ cells/cm in hES cell medium containing DMEM, 1% non-essential amino acids (100 µM), 1× penicillin/streptomycin, 2 mM L-glutamine, 10% FBS, 1% ITS, and β-mercaptoethanol (Gibco). Alternatively, ESI hES-2 may be used in place of ESI-017. For dissociation of the aggregates for seeding onto the microcarriers, the hES cell colonies were gently dissociated with 1.25 mg/ml of a collagenase mixture (NB6, Serva) for at least 4 minutes. The collagenase was rinsed away with PBS and replaced with hES cell medium. The entire surface area of the plate was then streaked with a 2 ml disposable plastic pipette at approximately 2 mm intervals. The resulting aggregates were then collected by scraping with a rubber policeman and transferred to a 15 ml falcon tube. The aggregates were pelleted in a centrifuge, resuspended in hES cell medium, and transferred to the plate or flask containing the pre-equilibrated microcarriers. The aggregates were seeded at approximately $5 \times 10^5$-$1 \times 10^6$ cells per well in 6 well plates, or between $1$-$2 \times 10^7$ cells per spinner flask. The hES cell aggregate/microcarrier mixtures were then incubated at 37° C. with no agitation. Medium was changed daily with fibroblast-conditioned hES cell medium unless specified. FIG. 7A shows the expansion of the hES cells in the clump based, aggregate culture system and the culture population was highly pluripotent as analysed by flow cytometry (FIG. 7B). Further the expansion in two types of culture medium was compared. Approximately 750 000 cells were seeded into each well of a 6 well dish with 100 mg Hillex II microcarriers in 3 ml human fibroblast conditioned 20% KOSR medium. The cells/beads were removed at the indicated time and assayed for cell number (attached and free). FIG. 8A showed that approximately 50% of the cells attached to the beads, and after a 1 day lag phase, began proliferation through the attachment and recruitment of beads into large cell/bead clusters. Similarly 6 well plates set up but with fibroblast conditioned DMEM+FBS medium had no significant impact on the cell attachment or growth compared to fibroblast conditioned 20% KOSR medium (FIG. 8B). The growth kinetics of the hES cells in the aggregate system at various time points in a multi passage expansion showed that the majority of the cells attached within the first 6 hours followed by a decline in the attachment rate (FIG. 9A) indicating a diverse population of cells from large clumps, small clumps and single cells. This variability in the cell population does not satisfy the first order kinetics (FIG. 9B) as described in Example 7 and as shown in FIG. 4A. FIG. 10 shows the growth kinetics of the hES cells when co-cultured with human fibroblasts (FIG. 10A) or in the absence of feeder cells (FIG. 10B) in a single passage expansion. The growth profile showed an initial loss of cells after passaging, followed by a lag pahse, exponential phase, a plateau.

B) Single-Cell Suspension Cultures.

Tri-methylamine microcarriers, Hillex II were pre-equilibrated as described above. Input hES cells were collected from cultures which had been prepared by single-cell suspension passaging on mitotically inactive human fibroblasts for at least 10 passages. For microcarrier seeding, confluent hES cells were dissociated with a 5 minute enzymatic treatment (TrypLE, Invitrogen). The cells were then titrated with a 5 ml pipette, and passed through a 70 µm cell strainer to remove any remaining clumps. The TrypLE was removed by pelleting the cells and aspirating the supernatant. After quantification with a haemocytometer, the cells were seeded at a density of $5 \times 10^5$ cells per well in 6 well plate with the pre-equilibrating microcarriers. The plate was incubated at 37° C. with no agitation. Medium was changed daily using fibroblast-conditioned hES cell medium unless specified. TrypLE-dissociated cells were inoculated into 6 well tissue culture plates coated with the indicated matrix; fibroblast feeders, fibronectin, conditioned fibroblast matrix, or nothing (TC plastic). Individual wells were dissociated and counted at the indicated times. Attachment and growth was efficient for the cells cultured on fibroblast feeders, fibronectin, and conditioned matrix (FIG. 11A). In general, the cells did not adhere to the uncoated tissue culture plastic. Photomicrographs of the wells showing the morphology of the cells indicated that the adherent cells grew as clusters which over time became confluent (FIG. 11B). The cells cultured long-term under single cell suspension passaging regimes maintained the pluripotencey marker Oct-4 (FIG. 11C).

The efficacy of various microcarriers as support surface was analysed following the transferring of the microcarrier particles into the individual wells of a 6 well plate at a density of 100 mg/well. One million cells per well were inoculated and the mixture was cultured in human fibroblast conditioned KOSR culture medium. Low or moderate affinity was seen for the microhex and cytodex 1 beads, Solohill FACT and Solohill Hillex II beads showed high affinity and Solohill Collagen beads showed moderate affinity (FIG. 12). Therefore adhesion and growth was specific to certain types of microcarriers and not a general phenomenon.

Finally it is to be understood that various other modifications and/or alterations may be made without departing from the spirit of the present invention as outlined herein.

Future patent applications may be filed on the basis of or claiming priority from the present application. It is to be understood that the following provisional claims are provided by way of example only, and are not intended to limit the scope of what may be claimed in any such future application. Features may be added to or omitted from the provisional claims at a later date so as to further define or re-define the invention or inventions.

REFERENCES

1. Chen G., Ushida T., Tateishi T., 2000; Hybrid Biomaterials for Tissue Engineering: A Preparative Method for PLA or PLGA-Collagen Hybrid Sponges; Adv. Mat. 12:6: 455-457.
2. Himes V B., Hu W., 1987; Attachment and growth of mammalian cells on microcarriers with different ion exchange capacities; Biotechnol and Bioeng. 29:9: 1155-1163.
3. Levine D W., Wang D I C., Thilly W G., 1979; Optimization of growth surface parameters in microcarrier cell culture; Biotechnol. and Bioeng. 21:5:821-845.
4. U.S. Pat. No. 6,875,607.
5. U.S. patent Ser. No. 11/298,208.

The invention claimed is:

1. A method of promoting the attachment, survival and/or proliferation of substantially undifferentiated stem cells in culture, the method comprising culturing the stem cells on a positively-charged support surface, wherein the stem cells express Oct4, Tra-1-60 and SSEA4.

2. The method according to claim 1, wherein the support surface further comprises an extracellular matrix protein.

3. The method according to claim 2, wherein the extracellular matrix protein is selected from the group consisting of elastin, fibronectin, vitronectin, tenascin, laminin, entactin, aggrecan, decorin, collagen I, collagen III, collagen IV and collagen VI, biologically active fragments or variants of said proteins, and combinations thereof.

4. The method according to claim 1, wherein the stem cells are human embryonic stem cells.

5. The method according to claim 1, wherein the support surface is a surface of a cell culture vessel selected from the group consisting of a tissue slide, a microscope slide, a flask, a plate, a multi-well plate, a bottle, a bioreactor, a two or three-dimensional scaffold, a tube, a suture, a membrane, a film, a microcarrier bead, a tissue and an organ.

6. The method according to claim 1, wherein the positively-charged support surface comprises a positively-charged molecule bound thereto and wherein the positively-charged molecule is selected from the group consisting of cationic trimethylamine, polyetherimide, poly-L-lysine, poly-D-lysine, poly-L-ornithine, poly-D-ornithine, poly(vinylamine), poly(allylamine), and combinations thereof.

7. The method according to claim 1, wherein the support surface is the surface of a microcarrier bead.

8. A method for identifying a test sample containing an agent or factor that modulates the differentiation of substantially undifferentiated stem cells, the method comprising the steps of:
   (a) contacting the substantially undifferentiated stem cells with (i) a positively-charged support surface and (ii) a test sample comprising a differentiation factor or agent; and
   (b) measuring the differentiation of the stem cells compared to the differentiation of similar stem cells in a culture in the absence of the test sample.

9. The method according to claim 8, wherein the support surface is a surface of a cell culture vessel selected from the group consisting of a tissue slide, a microscope slide, a flask, a plate, a multi-well plate, a bottle, a bioreactor, a two or three-dimensional scaffold, a tube, a suture, a membrane, a film, a microcarrier bead, a tissue and an organ.

10. The method according to claim 8, wherein the support surface includes a positively-charged molecule bound thereto.

11. The method according to claim 8, wherein the support surface further comprises an extracellular matrix protein.

12. The method according to claim 8, wherein the stem cells are human embryonic stem cells.

13. The method according to claim 8, wherein the support surface is the surface of a microcarrier bead.

* * * * *